United States Patent [19]
Ritzer et al.

[11] 4,450,282
[45] May 22, 1984

[54] CATALYST FOR A PROCESS FOR PRODUCING SILICONES

[75] Inventors: Alan Ritzer, Sand Lake; Heine Lapidot, Latham, both of N.Y.

[73] Assignee: General Electric Company, Waterford, N.Y.

[21] Appl. No.: 288,175

[22] Filed: Jul. 29, 1981

[51] Int. Cl.$^3$ .............................................. C07F 7/16
[52] U.S. Cl. ................................................... 556/472
[58] Field of Search ....................................... 556/472

[56] References Cited
U.S. PATENT DOCUMENTS 2,383,818  8/1945  Rochow et al. ............... 556/472
2,464,033  3/1949  Gilliam ............................ 556/472
3,133,109  5/1964  Dotson .
4,218,387  8/1980  Maas et al. .
4,250,290  2/1981  Petersen .
4,281,149  7/1981  Shade .

Primary Examiner—Paul F. Shaver
Attorney, Agent, or Firm—Heslin & Watts

[57] ABSTRACT

An improved direct process for producing organohalosilanes and particularly diorganodihalosilanes from silicon metal and an organohalide comprising contacting the two reactants in the presence of a partially oxidized copper catalyst having a surface area of at least 3.5 $m^2/gm$ and wherein 100% of the particles are less than 35 microns in size and wherein 100% of the particles are over 0.7 microns in size.

39 Claims, 3 Drawing Figures

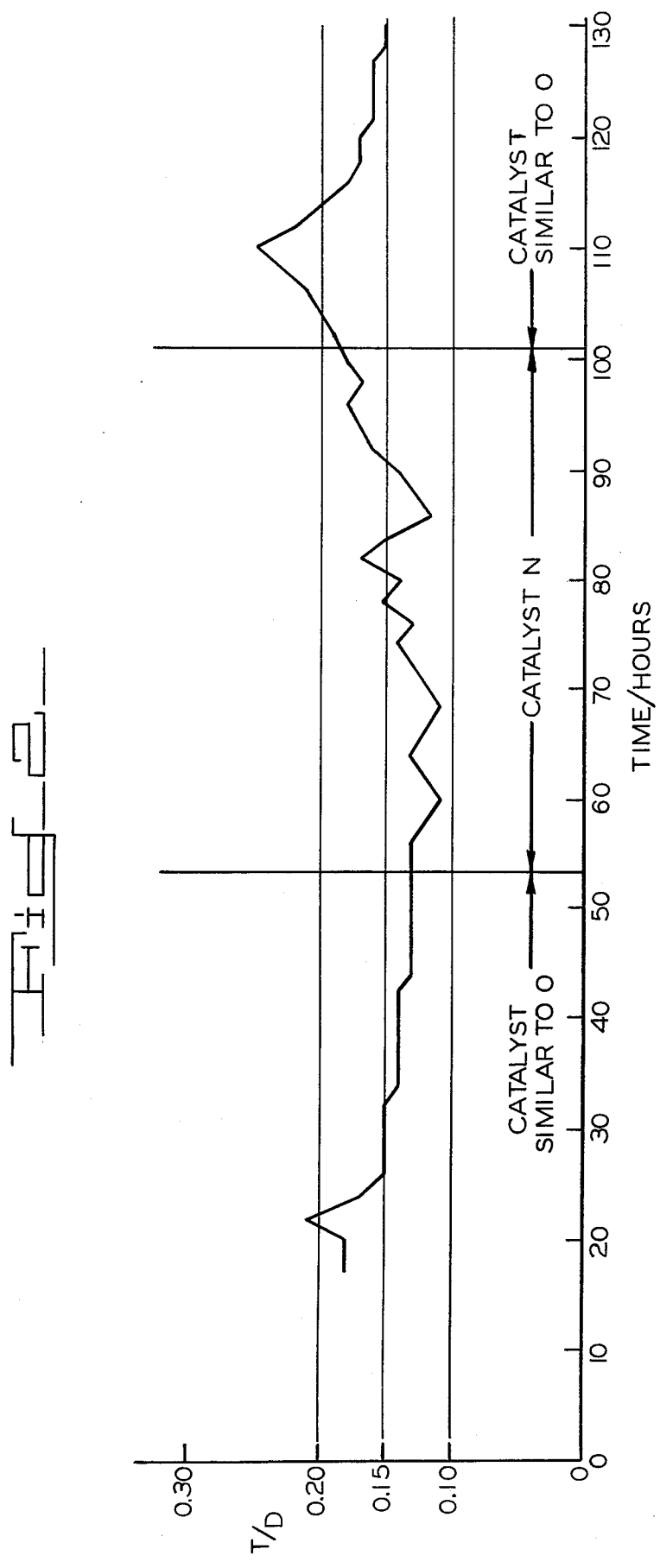

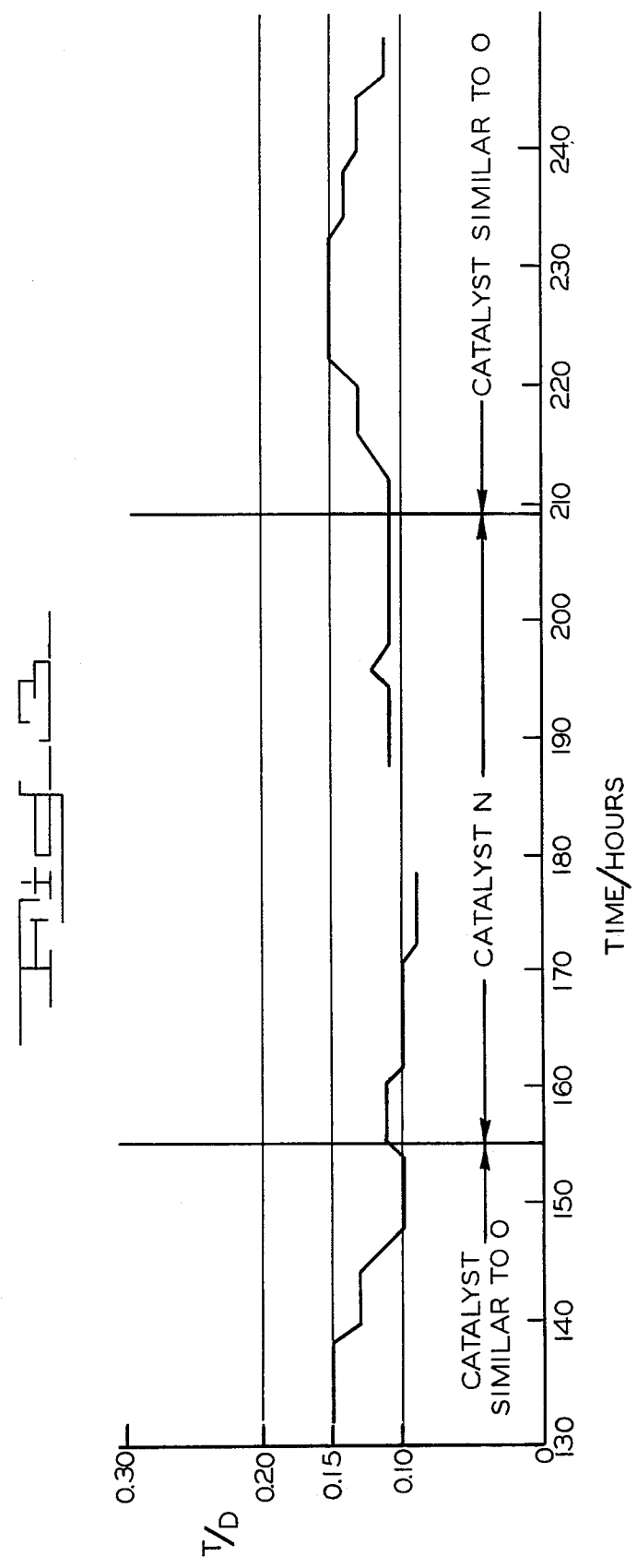

CATALYST FOR A PROCESS FOR PRODUCING SILICONES

BACKGROUND OF THE INVENTION

The present invention relates to a process for producing silicone compounds and more particularly the present invention relates to a catalyst in the basic process for producing organo silanes, the basic material to make silicone compounds.

The basic process for producing silicones generally comprises reacting an organohalide in the presence of a catalyst with silicon metal to produce organohalosilanes. The organohalide can be for instance methyl chloride, phenyl chloride, vinyl chloride and other organohalides. The silicon metal is preferably present in the form of silicon particles of relatively high purity, that is silicon material comprising at least 95% of silicon.

The catalyst that is preferred in most processes is a partially oxidized copper metal catalyst in the form of a powder. This basic process is disclosed in Rochow U.S. Pat. No. 2,380,995 which is hereby incorporated by reference. By means of this process there is produced a mixture of organohalosilanes which from a methyl chloride reactant the products can be for instance, $Me_2SiCl_2$, $Me_4Si$, $Me_3SiCl$, $MeSiCl_3$, $SiCl_4$, $HSiCl_3$, $MeHSiCl_2$, $Me_2HSiCl$. Although most of these products find some use, the most preferable is dimethyldichlorosilane, $Me_2SiCl_2$.

Normally, the process results in a sizable yield of organohalosilanes. Fortunately, most of this yield is in a form of $Me_2SiCl_2$, that is dimethyldichlorosilane or broadly, diorganodichlorosilane and also $MeSiCl_3$ which broadly is organotrichlorosilane. While the organotrihalosilane or methyltrichlorosilane have certain utilities by far it is preferred to maximize the yield of dimethyldichlorosilane. While the monomethyltrichlorosilane has limited uses in the production of silicone resins and in the production of trifunctional fluids, the diorganodichlorosilane (difunctional) silane is most preferred since it can be utilized to produce a variety of silicone products. For instance, it can be utilized as an ingredient in the production of silicone resins. However, by far its most prevalent use is as an intermediate in the production of linear diorganopolysiloxane polymers of wide viscosity range; that is, polymers in the viscosity range 100 to 10,000,000 centipoise and polymers in the viscosity range of 1,000,000 to 300,000,000 centipoise at 25° C.

These higher viscosity polymers are normally referred to as gums and are utilized as the base polymer in the production of heat vulcanizable silicone rubber compositions. The linear low viscosity fluids, when they are for example triorganosiloxy end-stopped, can be utilized as base fluids in the production of various silicone greases and various other types of silicone fluids. It should be noted above and below that while the discussion may be in some cases with respect to methyl, the same comments apply to cases where the organo group in the organohalosilane product of the basic silicon reaction is other than methyl, such as phenyl, vinyl, etc.

One broad use of such diorganodichlorosilanes is in the production of silanol end-stopped diorganopolysiloxane polymers of a viscosity varying from 100–1,000,000 to 10,000,000 centipoise and preferably from 100–1,000,000 centipoise at 25° C. Such silanol terminated polymers are utilized in the production of various types of room temperature vulcanizable silicone rubber compositions, both of the one-component type and the two-component type. An example of such linear triorganosiloxy end-stopped diorganopolysiloxane polymers in heat vulcanizable silicone rubber compositions is, for instance, disclosed in the DeZuba et al, U.S. Pat. No. 3,730,932 which is hereby incorporated by reference. An example of the silanol terminated polymers which are produced again by the further processing of the diorganodihalosilanes such as dimethyldichlorosilane is, for instance, disclosed in Beers U.S. Pat. No. 4,100,129 and Peterson, U.S. Pat. No. 4,250,290 which are hereby incorporated by reference.

These latter two patents disclose the use of the base silanol terminated polymers utilized to produce room-temperature vulcanizable silicone rubber compositions and the process of producing such base silanol polymers from the diorganodihalosilane. The foregoing U.S. Pat. No. 4,100,129 is just an example of one type of room-temperature vulcanizable silicone rubber composition that can be produced from such silanol polymers. There are many types of such compositions.

Basically speaking, the polymers produced can be both of the room temperature vulcanizable and of the heat vulcanizable types. The diorganodihalosilanes are first hydrolyzed with water, and then there is added to the hydrolyzate an alkali metal catalyst and the resulting mixture heated at elevated temperatures (that is, temperatures above 150° C.). Accordingly there is preferentially distilled and collected overhead cyclotetrasiloxanes. These cyclotetrasiloxanes are collected in a relatively pure form and then they are reacted in one particular type of process; either with triorganosiloxy chain stoppers or with water in the presence of an alkali metal hydroxide catalyst at elevated temperatures so as to produce linear polymers. The foregoing exemplary patents have been given above and the method of producing such polymers is well known in the art. Proceeding to the initial reactions, that is, in the production of the diorganodihalosilane, there have been various improvements on the Rochow process as exemplified by the following patents. One of the improvements is that of Dotson U.S. Pat. No. 3,133,109 which discloses the utilization of a jet mill to comminute the silicon particles as utilized in a fluidized bed reactor so as to increase the yield of organohalosilanes from the silicon metal. Another example of increasing the yield of the basic Rochow process is, for instance, the disclosure of R. Shade, U.S. Pat. No. 4,281,149 which discloses the abrading of certain of the silicon particles from the fluidized bed so as to increase overall process silicon utilization. Another example of an improvement is that disclosed in Ritzer et al, patent application Ser. No. 209,635, now U.S. Pat. No. 4,307,242 which is hereby incorporated by reference, which discloses the classification of certain of the particles that are taken out of the fluidized bed of the reactor and recycled for the purpose of increasing the yield of the desired product that is obtained from the silicon particles in the fluidized bed of the reactor. Accordingly, some of the work that has been done as disclosed above is so as to increase the amount of general product that is obtained in terms of the silicon metal that is fed into the reactor.

Further, the reactor can be either a stirred-bed or a fluidized bed reactor. However, it has been found that the maximum yield is obtained from the process by the use of a fluidized bed reactor utilizing gaseous organohalides, silicon metal and copper catalyst as small particles.

In addition, another approach in maximizing the desirable yield from the reaction has been to study the means by which the yield of diorganodihalosilane is maximized from a given quantity of silicon metal and copper catalyst. It is normally desirable to obtain as low a T/D ratio (T being the mono-organotrihalosilane and D being the diorganodihalosilane) as possible. One method of trying to increase such yield of diorganodihalosilane corresponding to the respective yield of mono-organotrihalosilane from the Rochow or direct process, has been the development of an efficient catalyst which maximizes such a yield. Traditionally, there has been utilized a copper catalyst usually modified with a promoter such as zinc. Performance varied markedly with the initial form of the copper. Generally, such copper catalysts were made from cemented copper, produced by the copper cementing process, containing free copper, copper oxides, several impurities such as, for instance, iron, tin, aluminum, lead, etc.

An example of one attempt to improve over such a copper catalyst for the direct Rochow process is, for instance, disclosed in Maas et al. U.S. Pat. No. 4,218,387 which is hereby incorporated by reference. This patent emphasized the production of a copper oxide catalyst for the direct process by the partial oxidation of copper produced by various means such as the cemented copper process. It should be noted that this patent emphasizes that only partial oxidation is to take place in the formation of the catalyst and not complete oxidation and the reference based the beneficial results of the catalyst (or the process by which it is prepared) in terms of utilizing a partially oxygenated atmosphere for the oxidation; i.e., gas with an oxygen partial pressure less than that of air and the absence of a reducing atmosphere in the oxidation gasses utilized to produce the copper catalyst of Maas et al. However, while this catalyst, was an improved catalyst it still was not as effective as would be desired. Further, the process of the preparation of this catalyst did not pay sufficient attention to the physical characteristics of the copper catalyst particles. In addition, there was the presence of certain oxides as well as copper metal in certain concentrations in the copper catalyst. Accordingly, it was highly desirable to produce a copper catalyst for utilization in the direct process which was an improvement over that of the prior art as well as that of the Maas et al patent which would result in improved yields of diorganodihalosilanes.

FIGS. 2 and 3 are plots of T/D versus time for some of the runs of Example 2 as will be explained below.

Figure 1:
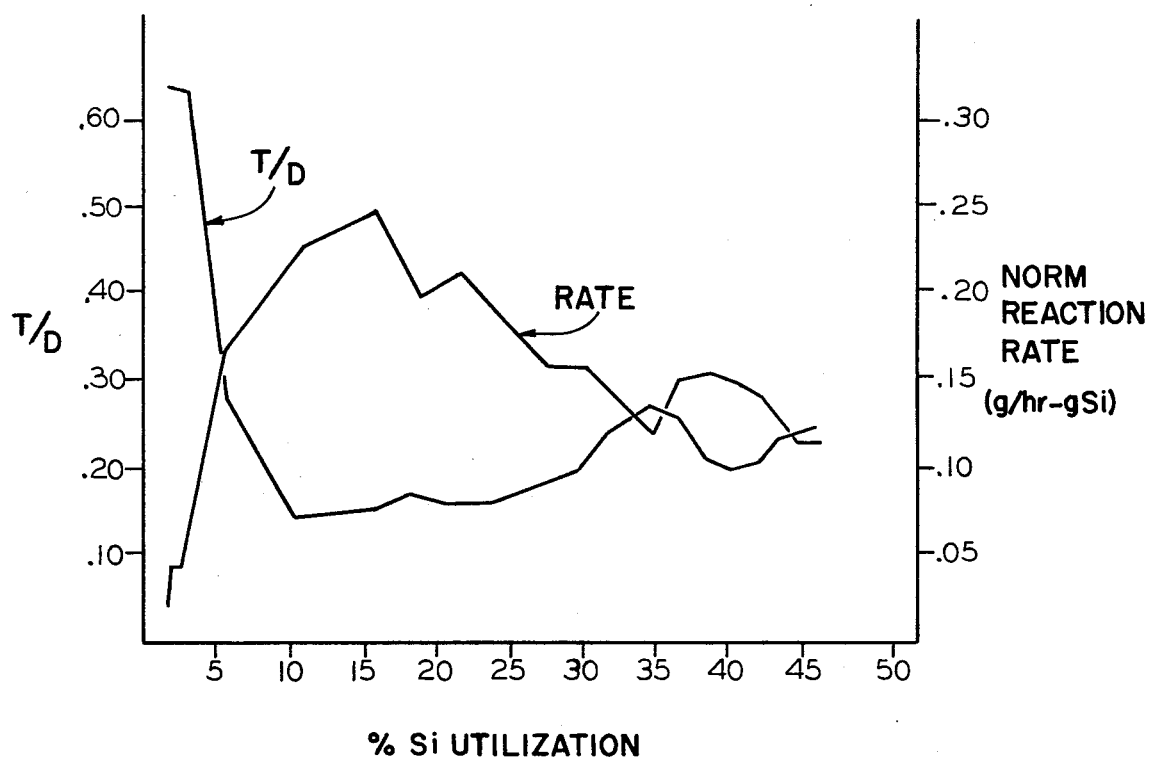
FIG. 1 is a plot of the T/D ratio, and reaction rate versus percent silicon utilized, of a typical copper catalyst as generated in laboratory batch testing.

It is one object of the present invention to provide an improved copper catalyst for the basic process for producing organohalosilanes from silicon metal and organohalides.

It is an additional object of the present invention to provide for a process for improving the yield of diorganodihalosilanes versus other reaction products in the process for producing organohalosilanes from silicon metal and organohalides.

It is still an object of the present invention to provide for an improved process utilizing a copper catalyst of a high surface area such that improved yields of diorganodihalosilanes are obtained from the basic process for producing organohalosilanes from silicon metal.

It is yet an additional object of the present invention to provide for an improved process for utilizing an improved copper catalyst which increases the yield of diorganodihalosilane versus mono-organotrihalosilane from the direct process for producing organohalosilanes by the reaction of organohalides with silicon metal.

These and other objects of the present invention are accomplished by means of the disclosures set forth herein below.

SUMMARY OF THE INVENTION

In accordance with the above objects and disclosure, there is provided by the present invention an efficient process for producing diorganodihalosilanes, comprising (1) passing an organohalide in contact with a silicon metal in the presence of a catalyst comprising partially oxidized copper particles having a surface area of at least 3.5 m$^2$/gram as determined by the Brunauer, Emmett, and Teller nitrogen adsorption method, and (2) removing the product stream of organohalosilanes from the reaction area where the organo group is a monovalent hydrocarbon radical and halo is halogen. Although the organohalide can be any organic halide, most usually, it is methyl chloride, phenyl chloride or vinyl chloride. Along with the surface area of the particles it is important, in utilization of the preferred catalyst within the scope of the invention that the particle size distribution of particles be such that 100% of the particles are less than 35 microns diameter in size and 100% of the particles are greater than 0.7 microns diameter in size.

It should be noted that the symbol $\mu$m stands for microns. Further, in the particle size distribution of the particles, it is important that the 50 percentile of the particle size distribution is in the range of 4–7 microns and the area mean diameter of the particles varies from 3.0 to 5.5 microns. The most important criteria of the copper catalyst that is utilized in the process of the instant invention, as far as identifying the characteristics of the catalyst, is its surface area. As a result of the utilization of the preferred catalyst of the process of the present invention, there results a reaction product from the process in which the weight ratio of organotrihalosilanes to diorganodihalosilane is less than 0.2 and is more preferably less than 0.1. A more detailed description of the process of the present invention will be given herein below.

DESCRIPTION OF THE PREFERRED EMBODIMENT

Before proceeding to discussion of the type of catalyst that is utilized as a preferred catalyst in the process of the instant case, it is necessary to discuss the general process. As noted before, the process can be carried out in a fixed bed reactor, in a stirred bed reactor or in a fluidized bed reactor. The fixed bed reactor is a column with the silicon particles therein where the methylchloride gas is passed therethrough. A stirred bed is like a fixed bed in which there is mechanical agitation of some sort so as to keep the bed in constant motion. A fluidized bed reactor, on the other hand, is a bed of silicon particles and copper catalyst particles which is, fluidized; that is the silicon particles are suspended in the gas that is passed through the reactor. The gas that is passed through the reactor is an organohalide, where the halide is, in most cases, chlorine and where the organo group can be any monovalent hydrocarbon radical, including fluoroalkyl groups. Thus preferably the organohalide has the formula RCl where R is a monovalent hydrocarbon radical. The R group can be independently selected from alkyl radicals of 1-8 carbon atoms, such as methyl, ethyl, propyl, etc.; mononuclear aryl radicals such as phenyl, methylphenyl, ethylphenyl, etc.; alkenyl radicals such as vinyl etc.; cycloalkyl radicals such as cyclohexyl, cycloheptyl, etc. Any monovalent hydrocarbon constituent group which is well known can be utilized. Preferably the organic group or the R group is an alkyl radical of 1-8 carbon atoms or phenyl, most preferably methyl.

The organic chloride which is passed or subjected to the direct process in the fluidized bed reactor is heated to the temperature above its boiling point; such that it is converted to the gas and then passed in the form of a gas at sufficient rate through the column so as to fluidize the bed of silicon particles and the catalyst particles in the column. The fluidized bed is substantially made up of silicon and catalyst particles. The silicon particles are composed of silicon metal which is present in the form of particles having a size in the range of 10 to 700 microns, with an average size of greater than 20 microns and less than 300 microns in size. The mean diameter of the silicon particles is preferably in the range of 100 to 150 microns. Silicon metal is usually obtained at a purity of 98% by weight of silicon and it is then comminuted to particles of silicon metal in the foregoing range, described above for utilization in the fluidized bed reactor. When it is ground down to the proper size it is fed into the silicon fluidized bed reactor as needed. It should be noted that the process of the instant case can be utilized in any type of reactor such as the fixed bed, the stirred, and the fluidized bed reactors. Most preferably the fluidized bed reactor is utilized since the maximum selectivity and the maximum amount of diorganodihalosilane is obtained with a fluidized bed reactor. The process of the instant case is carried out at a temperature in the range of 250° to 350° C., and more preferably, at a temperature range of 280° to 350° C. At this thermal condition, the maximum selectivity in terms of the formation of diorganodihalosilane, as well as the maximum conversion of organohalide with the silicon metal, is obtained as well as the maximum rate of conversion. It is also advisable to carry out the process under pressure since this increases the yield, that is, the maximum conversion of organohalide to diorganodihalosilanes. It is generally desired to have the process carried out under 1-10 atmospheres of pressure and more preferably at a pressure of 1-5 atmospheres of pressure gauge; that is, pressure above atmospheric pressure. Under these conditions, there is fed into the reactor the desired amount of silicon metal as needed as well as the desired amount of copper catalyst. Organohalide gas is continually passed through the reactor so as to fluidize the silicon particles, and the copper catalyst particles and there is passed out of the reactor the product organohalosilane gas as well as the unreacted organohalide. These mixtures of gasses, along with small particles of silicon metal and copper catalyst, are passed out of the fluidized reactor and are passed through one or more cyclones so as to separate the larger particles of materials from the product gas stream. These particles can be returned to the reactor for further utilization in the process so as to maximize the yield of the desired product from the silicon metal. Smaller particles are passed out with the product stream and the stream is subsequently condensed. The unreacted organohalide is separated by distillation. The purified organohalide is heated to convert it to a gas and then recycled through the fluidized reactor for the further production of organohalosilanes. The crude organohalosilanes product stream is passed through a distillation column so as to distill out, in pure form, the various fractions of chlorosilanes that have been produced by the process. It is necessary to distill and purify the diorganodihalosilanes and the other chlorosilanes so that they can be utilized in the process for producing silicone materials, as has been discussed previously. This is the general process in which the preferred catalyst of the present invention is utilized in order to produce organohalosilane compounds.

It should be noted that the process may be varied as explained above. For instance, as pointed out in Dotson, U.S. Pat. No. 3,133,109 there may be utilized a jet mill at the bottom of the fluidized bed reactor or connected to the fluidized bed reactor so as to take the larger particles of silicon metal, and copper catalyst, and comminute them so as to produce finer particles of silicon metal and copper catalyst which can further react in the reactor to produce the desired organohalosilanes. Another preferred method of obtaining further utilization of the silicon metal in the reactor is to take the smaller particles or correspondingly the particles of silicon metal that have been utilized to the greatest extent in the reactor and pass them through an abrading operation so as to clean the surface or form a clean surface on the silicon particles so that the silicon particles are capable of further reaction in the process of the instant case. This particular operation or treatment of the smaller silicon particles, as well as the large silicon particles, and copper catalyst particles is disclosed in the Shade U.S. Pat. No. 4,281,149 which is hereby incorporated by reference. Generally such an improvement as that disclosed in the foregoing patent comprises taking the smaller silicon particles and copper catalyst alloy and further abrading them so that the coating of the particles is removed, or some of the coating is removed, and a clean surface on the small particles of silicon metal is presented for further reaction in the fluidized bed reactor. This is advantageously done by taking the smaller particles out of the fluidized bed reactor, abrading them to remove the coating, and then returning the particles to the fluidized bed reactor. Another improvement is disclosed in Ritzer Ser. No. 209,635 which results in the utilization of as much silicon metal for the conversion of organohalosilanes as was possible at the time of the invention of the foregoing Ritzer application. This further improvement comprises the selective separation of the finer or smaller particles of silicon metal and copper catalyst from the reactor by the use of cyclones and classification of the sizes and then returning certain of these particles back to the reactor for further utilization in the process for producing organohalosilanes. It should be noted that this process of the Ritzer et al disclosure varies from the earlier disclosure of Dotson U.S. Pat. No. 3,133,109 which disclosed the taking of the larger particles of silicon metal and comminuting them so as to breakup the particles to smaller particles which could react further in the process of producing organohalosilanes. Thus, the Dotson process could be carried out directly in the reactor while it was advantageous to carry out the processes of Shade and Ritzer et al, preferably outside of the reactor. Needless to say, any of these three processes were improvements on the basic process in their further utilization of the basic silicon metal. All of these three processes can be utilized in the present process in that their main function is to increase the yield of organohalosilanes from the basic silicon metal that is utilized. However, in the present case, while the yield from the silicon metal is the same, nevertheless, the advantage of the instant process is that there is obtained an improved selectivity; that is, a greater yield of diorganodihalosilane over monoorganotrihalosilane.

It must also be appreciated that once the copper catalyst and silicon metal particles are in the fluidized bed reactor, the copper catalyst fuses onto the silicon metal such that there result particles of a copper-silicon alloy whose characteristics have not as yet been fully defined. The study as to the composition and behavior of such copper-silicon alloy is still being carried out and is by no means complete. However, this work does not form the invention of the instant case and the work that has been done in terms of characterization of the copper-silicon alloy will not be addressed herein.

It is the invention of the instant case of the use in the direct process of a preferred copper catalyst, such that the selectivity or the T/D ratio is generally less than 0.2 after the incubation period and is preferably less than 0.1 after the initial activation period. The copper catalyst is preferably a cemented copper catalyst. It is produced by taking a solution of a copper compound and passing it over scrap iron which results in the passing into solution of some of the iron and the deposition on the scrap iron of copper in the form of a fine precipitate. This precipitate is then taken and subjected to a pyrometallurgical process which results in the partial oxidation of the cemented copper. The preferred copper catalyst for utilization in the process of the instant invention generally has some rather general specifications which should be observed but do not have to be adhered to strictly in all cases.

Thus, the total copper in the catalyst should be anywhere from 77 to 87% by weight and is preferably 83.0% as a minimum. The total reducing power of the catalyst should be 76.5 in the range of 70 to 90 and is more preferably 75 to 80. By reducing power, it is meant TRP or total reducing power as determined by titration with standard iron sulfate solution to abrupt end-point using Ferroin indicator. The total metallic copper content of the catalyst generally varies from 10-20% by weight and preferably 15-20% by weight.

It is also preferred that the catalyst have 30 to 50% by weight of copper as cuprous oxide and preferably 39 to 50% by weight of cuprous oxide and 30-50% by weight of cupric oxide and preferably 35 to 43% by weight cupric oxide. Generally, the chloride content should be in the range of 0 to 0.2%, more preferably 0 to 0.1% by weight and the sulfate content varied from 0 to 1.5% by weight, and more preferably from 0 to 0.8% maximum. Generally, the iron content of the copper catalyst can vary anywhere from 0 to 1.5% by weight and more preferably from 0 to 1.0% by weight and the lead content vary from 0 to 0.2% by weight, and more preferably from 0 to 0.15% by weight maximum. In the same way the tin content of the catalyst can be anywhere from 0 to 0.5% by weight and it is preferably 0.4% by weight maximum while the water content can vary from 0 to 0.75% by weight and is preferably 0.5% by weight maximum.

Although the above measurements are generally desired to be met by the copper catalyst, it should be noted that they are not the most important measurements for the preferred copper catalyst of the instant invention. Rather they are preferred measurements which are desired. If one or more of the measurements are not met by the catalyst, the catalyst can still be utilized in the instant invention. But if most of the measurements are not met, then the catalyst cannot be utilized in the instant invention. Other desirable measurements of the catalyst of the instant invention are that the apparent density should be in the range of 1.2-1.4 grams per cubic centimeter, and more preferably 1.24 to 1.32 grams per cubic centimeter, and the Fisher number should vary from 1.8 to 2.4 and more preferably vary from 1.9 to 2.0 microns. The Fisher number is a determination of the air permeability of a powder. This measurement is converted to an equivalent specific surface area or particle size by semi-empirical methods. It is explained, for example, in *AIChE Equipment Testing Procedure: Particle Size Classifiers* (1980). Again, the apparent density and the Fisher number are desirable specifications for the copper catalyst of the instant invention. If, in total, most of the other measurements as explained above have been met, then the catalyst can still be utilized in the process of the instant case with the advantageous results. If the proper catalyst does not meet the specifications of apparent density and the Fisher number by a small degree; that is, plus or minus 10%, nevertheless it could still be utilized if the rest of the measurements of the copper catalyst come within the above specifications ranges as given previously.

However, there is one measurement that the catalyst must meet, and that is it must have a surface area as determined by the BET test method; that is, the Brunauer, Emmett and Teller test method of surface area by nitrogen adsorption, and that is that the surface area of the catalyst be at least 3.5 meters square per gram. It should be understood that the references to surface area in the specifications and claims is surface area as determined by the Brunauer, Emmett and Teller Test Method. The surface area, as determined by this method, should not go above 12 meters square per gram and is preferably in the range of 3.7 to 8 meters per gram. The surface area should not go above 12 meters square per gram since the surface morphology changes sufficiently above that surface area. The above surface area is desirable if the copper catalyst is to have the advantageous selectivity mentioned previously. It has been found with the large surface area that such particles result in a faster reaction rate in the process of the instant case, as well as result in higher selectivity; that is, a lower T/D ratio of less than 0.1. To get this beneficial selectivity in the T/D weight ratio, it is not only desirable that the surface area of the particle be at least 3.5 meters square per gram, but it is also desirable that the particles have the proper particle size distribution. A measurement of particle morphology herein encompasses not only particle size distribution, but also the surface area of the particles of the copper catalyst. It is necessary to have the appropriate particle size distribution such that 100% of the particles of the copper catalyst are less than 35 microns and 100% of the particles are greater than 0.7 microns. It is also necessary that in the particle size distribution of the particles that is the 50th percentile of the particles be 4-7 microns in size, and more preferably, 4–5 microns in size. It is also desirable that the area mean diameter of the particles generally be in the area of 3–5.5 microns in size and more preferably 3–4 microns in size. The area mean diameter is preferably calculated by the formula $$d_{mean} = \left( \Sigma \frac{W_i}{d_i} \right)^{-1}$$

where $W_i$ is weight fraction of ith fraction of the particle size distribution, $d_i$ is equal to arithmetic mean diameter of particles of the ith fraction.

Of these measurements of particle size distribution, the most important, as far as the invention of the instant case is concerned, is the extreme particle size distribution; that is, that 100% of the particle be less than 35 microns and 100% of the particles be greater than 0.7 microns and the 50th percentile or median particle size criterion be met. Accordingly, as long as the copper catalyst meets the surface area criteria set forth above, as well as the extreme particle size distribution mentioned also above, it can be utilized in the instant invention with advantage even though the other aspects of the particle size distribution or the elemental analyses of the copper catalyst are not completely met; that is, as long as most of those measurements are met and the material has the surface area as determined by the BET method, as well as the particles are within the extreme ranges noted above, then it can be utilized in the instant invention with advantage.

Accordingly, utilizing such a catalyst and preferably one that meets all the specifications set forth above, there can be obtained a T/D weight ratio after the initial incubation period varying from 0.1 to 0.2 and more preferably varying from 0.06 to 0.15 with the most preferred value being less than 0.1. Such copper catalysts can be obtained from the Glidden Catalyst Metals Division of SCM Corporation, Cleveland, Ohio, or from American Chemet Corporation, Deerfield, Ill. Such catalysts are produced by a pyrometallurgical process applied to copper cement. It should be noted that the performance of a typical catalyst in a fluidized bed reactor is set forth in FIG. 1. FIG. 1 is a plot of the T/D ratio and the normalized reaction rate (relative to batch silicon metal consumption) versus the percent silicon utilized. As can be seen when the reaction initiates, the percent silicon utilized is at a low value and the T/D ratio is very high but as soon as 10% of the silicon has been utilized then the T/D ratio decreases to a desirable level, and stays about that level, and begins climbing slightly higher until about 45% of the silicon metal has been utilized. On the other hand, the rate starts at a very low level with the percent silicon utilized and increases to a maximum with about 15% silicon utilized, and then decreases to a stable value when about 35% silicon metal has been utilized. The T/D ratio also produces a reverse bell shaped curve with respect to reaction time in a reactor; that is, the T/D ratio starts at a high value and decreases to a low value after about 7½ to 10 hours of reaction time, and then starts increasing to a high level depending on the copper catalyst utilized as noted.

In the present invention, it is possible, after the reaction has proceeded after the incubation time of 460 minutes or 520 minutes, to obtain a T/D ratio of less than 0.1. It should be noted that FIG. 1 is not representative of the preferred catalyst of the instant case, but is generally shown to indicate a general T/D curve and the reaction rate curve versus percent silicon utilization. The process of the instant case follows this curve but the T/D values are lower within the ranges specified above. With the process of the instant case, it is possible to produce an organohalosilane product stream in which the T/D ratio after the incubation period of roughly 500 minutes is less than 0.1. It should also be noted that, even though, in the entire reaction, the T/D ratio is not always below 0.1 in the main part of the process, it will preferably be below 0.1 and results in maximum selectivity in the production of diorganodihalosilanes as compared to other processes with other catalysts.

With the production of diorganodihalosilanes and preferably dimethyldichlorosilanes, it is possible to produce a whole variety of resins and polymers. Thus, the dimethyldichlorosilane can be utilized as an ingredient in the production of silicone resins composed of trifunctionalsiloxy units and difunctionalsiloxy units. It can also be reacted or hydrolyzed in water so as to result in low molecular weight linear dimethylpolysiloxane polymers which are silanol end-stopped. These polymers are then taken, and there is added to them the desired amount of alkali metal hydroxide, catalysts such as sodium hydroxide and heated at temperatures above 150° C. to preferentially produce octamethylcyclotetrasiloxane. These tetrasiloxanes are taken in substantially pure form and there is added to them anywhere from 5 to 50 parts per million of KOH and the resulting mixture heated at temperatures above 150° C. from anywhere from 8 to 24 hours, in the presence of chain-stoppers such as hexamethyldisiloxane, divinyltetramethyldisiloxane, etc., to result in high molecular weight linear polymers. It should be noted that the smaller the amount of chain-stopper, the higher the molecular weight of the polymer, and the larger the amount of chain-stopper the lower the molecular weight of the polymer.

By the use of acidic catalysts such as acid treated clay sold by the Filtrol Corporation of Los Angeles, Calif., or acid treated carbon black, there can be produced fluids that are trimethylsiloxy, linear dimethylpolysiloxane fluids having a viscosity of anywhere from 1000 to 1,000,000 centipoise at 25° C. and these fluids can be utilized to produce greases, channel fluids, lubricants, etc. These materials will have all the advantages of silicones; that is, resistance to water, resistance to weathering, etc.

In the case where the alkali metal hydroxide catalyst is utilized, a small amount of chain-stopper is utilized and there is produced a high molecular weight gum, that is, a polymer having a viscosity of anywhere from 1,000,000 to 300,000,000 centipoise at 25° C. Such polymers can be taken and there can be incorporated into them both extending and reinforcing types of fillers, flame retardant additives and various other types of additives, and the composition cured with a peroxide catalyst at elevated temperatures over 100° C. to produce a silicone elastomer.

These polymers, with vinyl terminal units, can also be taken and reacted with hydroxide polysiloxanes in the presence of a platinum catalyst to produce silicone elastomers. Then tetrasiloxanes may also be taken and reacted with water or equilibriated with water in the presence of an alkali metal hydroxide catalyst to produce silanol terminated polymers, as a dimethylpolysiloxane polymer of a viscosity varying from 100 to 1,000,000 centipoise at 25° C. or higher. By the incorporation in such silanol polymers, an alkyl silicate or a partial hydrolysis product of an alkyl silicate and as a catalyst, a metal salt of carboxylic acid and preferably a tin salt of carboxylic acid there can be formed a two-component room temperature vulcanizable silicone rubber composition. That is, when all the ingredients are mixed, the composition cures at room temperature to a silicone elastomer. For example, such a composition is to be found disclosed in Lampe et al, U.S. Pat. No. 3,888,815.

One-component room temperature vulcanizable silicone rubber compositions can be formed also by taking silanol, dimethylpolysiloxane polymers and incorporating into them cross-linking agents which may be alkoxy functional cross-linking agents or acyloxy functional cross-linking agents. There is added to these ingredients a tin salt of carboxylic acid. The resulting composition is packaged in a single package in a substantially anhydrous state. When the seal on the package is broken and when exposed the composition applied to whatever shape desired and exposed to atmospheric moisture, the composition cures to a silicone elastomer at room temperature. In the case where the one-component RTV system has an alkoxy functional cross-linking agent, then the catalyst is preferably a titanium ester. When the cross-linking agent is an acyloxy functional silane or another type of functional silane, then preferably the catalyst is a tin soap. An example of such compositions are first to be found in Beers, U.S. Pat. No. 4,100,129. There can be added various ingredients to such one-component RTV systems as disclosed in the foregoing patents such as self-bonding additives, flame retardant additives, pigments, etc. It should also be noted that in the foregoing preferred process by which the organohalosilanes are produced, that preferably there are utilized 0.5 to 10 parts of copper catalyst per 100 parts of silicon metal and more preferably, 1 to 3 parts of copper catalyst per 100 parts of silicon metal. However, this range can vary by a wide margin since the reaction is carried out not in a batch process, but in a continuous process in which there is utilized a fluidized bed. Accordingly, the foregoing concentrations of copper catalysts and silicon metal is not a range that has to be adhered to strictly but has to be generally followed. In addition, the methylchloride gas is utilized in a large excess in the reaction since there is continually a fluidized bed with a stream of gasses, organohalide or methylchloride passing through the particles of silicon metal and the copper catalyst particles fluidizing them. The silicon metal and the copper catalyst particles are inserted into the reactor and spent copper catalyst, and silicon metal is taken out of the reactor as described previously, such that there is always approximately a constant volume of particles in the fluidized bed of silicon metal and copper catalyst particles present in the form of an alloy so as to produce the desired organohalosilanes.

The examples below are given for the purpose of illustrating the present invention and not given for any purpose of setting limits and boundaries to the instant invention. All parts in the examples are by weight.

EXAMPLE 1

There was set-up an experimental stirred-bed reactor in the laboratory which had the following specifications and was utilized for all experiments described herein.

The reactor system was comprised of a 1" internal diameter stainless steel tube approximately 18" long. It was equipped with dual zone electrical heaters such that the reaction zone (approximately 1" by 6" long) was maintained at desired isothermal condition. Further, the reactor internals were equipped with a helical stainless steel stirrer to maintain desired solids agitation. Appropriate mass flow metering of alkyl halide reactant was provided, as was a product recovery train to quantitatively recover organohalosilanes produced. These were subsequently analyzed compositionally by gas chromatography.

In the foregoing reactor there were tested various copper catalysts which are defined as A, B, C, D, E, F, G, H, I, J, below. The surface area of these catalysts is given in Table I below, as well as the incubation time, the time to reach steady state, as well as the average T/D ratio after incubation time.

In each case, the reactor was operated at 300° C. with a stirred bed in which was passed methylchloride in the bed of silicon metal, using one of the copper catalysts shown in Table I. In all cases, 0.44 wt. % zinc powder was added as a promoter. The reactor in each case was operated under one atmosphere of pressure and utilized silicon metal of a particle size of approximately 37-74 microns in size. There was utilized the foregoing catalysts in the range of 3 to 10 parts per 100 parts of silicon metal. The results are set forth in Table I.

TABLE I

| CATA-LYST | T/D | $(CH_3)_2SiCl_2$ IN CRUDE (Wgt. %) | INCUBATION TIME (MIN.) | TIME TO ST. STATE (MIN.) | NORM. Rx RATE (GM/HR. GM SI) | BET S.A. $(M^2/GM)$ |
|---|---|---|---|---|---|---|
| A | .120 | 85.5 | 530 | 400 | .064 | 5.2 |
| B | .104 | 87.1 | 580 | 400 | .037 | 1.0 |
| C | .188 | 77.1 | 480 | 510 | .032 | 1.6 |
| D | .192 | 77.4 | 820 | 770 | .040 | 2.7 |
| E | .138 | 83.9 | 1230 | 1600 | .020 | 3.6 |
| F | .085 | 88.6 | 460 | 150 | .136 | 4.1 |
| G | .250 | 77.4 | 900 | 770 | .018 | 2.5 |
| H | .136 | 84.6 | 190 | 1520 | .071 | 4.5 |
| I | .097 | 87.2 | 520 | 230 | .081 | 3.2 |
| J | .108 | 87.1 | 540 | 480 | .054 | 1.3 |

The data that was available on the foregoing catalysts set forth in Table I above are listed in Table III.

EXAMPLE 2

Some runs were made of the preferred catalyst of the instant invention as well as with catalysts that were not desirable. These runs were made in a commercial reacfor so as to determine the performance characteristics of the different catalysts.

Table II below presented a number of instances in which the use of catalysts of the preferred physical and chemical properties resulted in production stretches of improved product composition; i.e., lower T/D.

The reactors were of the fluidized bed type, with continuous feed of methyl chloride gas both as one of the reactants and as the fluidizing gas. The other reactant, silicon powder of particle size between 10 and 700 microns, was also fed continuously (or frequently enough to be essentially continuous feed). The catalyst was added periodically, in a proportion of 1 to 5% by weight of the silicon feed.

The operating conditions of the reactors were generally: temperature: 280°-305° C.; pressure: 28-38psig.

TABLE II

| CATALYST IDENTITY | LENGTH OF TIME USED, HRS. | AVERAGE T/D | RATE[1] | BET SURFACE AREA OF CATALYST[2] m²/g |
|---|---|---|---|---|
| A | 45 | 0.110 | 0.220 | 5.2 |
| A | 32 | 0.100 | 0.210 | 5.2 |
| B | 94 | 0.200 | 0.220 | 1.0 |
| G | 80 | 0.160 | 0.244 | 2.5 |
| M | 102 | 0.188 | 0.173 | 1.7 |
| N | 53 | 0.100 | 0.146 | 3.7 |
| N | 70 | 0.110 | 0.216 | 3.7 |
| O | 128 | 0.080 | 0.223 | 3.8 |

[1]Rate is expressed as a normalized rate (similar to that presented in the laboratory data of Table I):

$$\frac{\text{lbs. crude product}}{\text{(lbs. reacting mass)} \times \text{hr.}}$$

[2]Additional properties are presented in Table III.

All the catalysts within the scope of the instant invention that are set forth in Examples 1 and 2 had a particle size such that 100% of the particles were less than 35 microns in size and 100% were greater than 0.7 microns in size as determined by the Micro-Meritics Sedigraph, supplied by Micro-Meritics, Norcross, Ga. Further in the data of Table II and Table III show that catalysts with the desired surface area gave a low T/D ratio while catalysts with a small surface area gave a high T/D ratio. Table II has the approximate average T/D for the runs of Example 2 while FIGS. 2 and 3 are a plot of the detailed data of certain commercial runs. FIGS. 2 and 3 show a plot with catalysts within the instant invention. One of the catalysts has measured properties similar to catalyst O of Tables II and III. However, the catalysts are not the same. These plots are compared to runs with catalyst N which is a catalyst also within the scope of the instant invention and whose physical properties as well as the operating properties are set forth in Table II and Table III. The run was started with a catalyst similar to O and then catalyst N was inserted for a time in the reactor and then the catalyst similar to O was inserted in the reactor, etc. The runs were continuous. FIGS. 2 and 3 are just included to show a typical comparison of the T/D profile of catalysts of the instant invention in a commercial run.

TABLE III

Physical Data for Tables I and II

| Catalyst | TRP | Total Cu | Cu* | Cu₂O | CuO | App. Density (gm/cm³) | BET Surface Area m²/g | Part Size (μm) Median | Fisher Number |
|---|---|---|---|---|---|---|---|---|---|
| A | 73.20 | 83.4 | 14.47 | 40.64 | 41.40 | 1.27 | 5.2 | 4.6 | 2.20 |
| B | 104.8 | 88.5 | 20.1 | 59.6 | 19.4 | 1.59 | 1.0 | 6.6 | 3.70 |
| C | 53.00 | 85.20 | 1.55 | 49.00 | 49.55 | 1.29 | 1.6 | — | 3.10 |
| D | 15.20 | 79.80 | 1.40 | 12.00 | 84.78 | 1.60 | 2.7 | — | 3.85 |
| E | 44.80 | 81.72 | 6.57 | 30.00 | 60.72 | 1.45 | 3.6 | — | 1.85 |
| F |  | 82.06 | 12.33 | 33.96 | 49.54 | 1.36 | 4.1 | 6.0 | 3.35 |
| G | 76.80 | 83.2 | 15.81 | 41.23 | 38.58 | 1.65 | 2.5 | 5.8 | 3.25 |
| H | 77.90 | 84.0 | 16.78 | 40.14 | 39.48 | 1.24 | 4.5 | 4.6 | 2.15 |
| I |  | 82.5 | 10.0 | 38.2 | 48.3 | — | 3.2 | — | — |
| J |  | 83.80 | 8.55 | 46.52 | 42.48 | — | 1.3 | — | — |
| M |  | 83.46 | 8.5 | 47.7 | 40.8 | — | 1.7 | — | — |
| N | 76.63 | 83.5 | 16.68 | 39.07 | 40.18 | 1.43 | 3.7 | 6.6 | — |
| O | 73.50 | 83.55 | 15.10 | 39.52 | 41.75 | 1.23 | 3.8 | 4.5 | 2.00 |

What is claimed is:

1. An efficient direct process for producing organohalosilanes and particularly diorganodihalosilanes, comprising (1) passing an organohalide in contact with metal in the presence of a catalyst comprising partially oxidized copper particles having a surface areas of at least 3.5 meters square per gram as determined by the B.E.T. Method wherein the catalyst particles have a particle size distribution in which 100% of the particles are less than 35 μm and 100% of the particles are greater than 0.7 μm, and (2) removing a product stream of organohalosilanes from the reaction area where the organo group is a monovalent hydrocarbon radical.

2. The process of claim 1 wherein the total copper content of the catalyst varies from 77-87% by weight.

3. The process of claim 2 wherein the catalyst has 10-20% by weight of metallic Cu, 30-50% by weight of Cu₂O, and 30-50% by weight of CuO.

4. The process of claim 3 wherein the catalyst has 0-0.2% by weight chloride, 0-1.5% by weight sulfate, 0-1.5% by weight iron, 0-0.2% by weight lead, 0-0.5% by weight tin and 0-0.75% by weight water.

5. The process of claim 4 wherein the total reducing power of the catalyst varies from 70-90.

6. The process of claim 5 where the catalyst should have an apparent density in the range of 1.2-1.4 grams per cubic centimeter, and a size number as determined by the Fisher Method in the range of 1.8-2.4 μm.

7. The process of claim 6 wherein the catalyst particle size distribution is such that the particles in the 50 percentile of the particle size distribution are in the range of 4-7 μm and area—mean diameter of the particles is in the range of 3.0-5.5 μm.

8. The process of claim 7 wherein the halogen of the organohalide is chlorine.

9. The process of claim 8 wherein organohalide has the formula

RCl where R is selected from the class consisting of alkyl radicals of 1–8 carbon atoms, aryl radicals and alkenyl radicals of 2–8 carbon atoms.

10. The process of claim 9 wherein the organohalide is methyl chloride and is present in the form of a gas.

11. The process of claim 10 wherein the silicon metal is present in the form of particles having a size in the range of 10–700 microns.

12. The process of claim 11 wherein the silicon metal particles have a mean particle size distribution of greater than 20 μm to less than 300 μm.

13. The process of claim 12 wherein the reaction is carried out at a temperature of 250°–350° C.

14. The process of claim 13 wherein the process is carried out at pressures of 0–10 atmospheres above atmospheric pressure.

15. The process of claim 14 wherein the catalyst particles and the silicon metal particles are present in a reactor as a fluidized bed and organohalide gas is forced therethrough and then is removed from the fluidized bed a product stream of unreacted organohalides and organohalosilanes.

16. The process of claim 15 wherein in the organohalosilanes reaction product stream, the main constituents are organotrihalosilane and diorganodihalosilane where the weight ratio of organotrihalosilane to diorganodihalosilane is less than 0.2 where organo is as previously defined.

17. The process of claim 16 wherein the weight ratio of organotrihalosilane to diorganodihalosilane in the product stream is less than 0.1.

18. The process of claim 17 wherein the product stream of organohalosilanes is passed through particle entrapment units to remove particles of silicon and catalyst wherein the larger particles are returned to the reaction zone and to where the product stream is then condensed and distilled to separate and purify the different fractions of organohalosilanes.

19. The process of claim 17 wherein the particle entrapment units are cyclone particle separators.

20. An efficient direct process for producing organohalosilanes and particularly diorgandihalosilanes in which there is contacted an organohalide with silicon metal in the presence of a particularized, partially oxidized copper catalyst and there is removed from the reaction area a product stream of organohalosilanes where the organo group is a monovalent hydrocarbon radical characterized in the improvement, comprising, in that, the particularized copper catalyst has a surface area of at least 3.5 meters square per gram as determined by the B.E.T. Method.

21. The process of claim 20 wherein the total copper content of the catalyst varies from 77 to 87% by weight.

22. The process of claim 21 wherein the catalyst has 10 to 20% by weight of metallic copper, 30–50% by weight of Cu$_2$O, and 30–50% by weight of CuO.

23. The process of claim 22 wherein the catalyst has 0–0.2% by weight of chloride, 0–1.5% by weight of sulfate, 0–1.5% by weight of iron, 0–0.2% by weight of lead, 0–0.5% by weight of tin, 0–0.75% by weight of water.

24. The process of claim 23 wherein the total reducing power of the catalyst varies from 70 to 90.

25. The process of claim 24 wherein the catalyst should have an apparent density in the range of 1.2–1.4 grams per cubic centimeter and a number as determined by the Fisher method in the range of 1.8–2.4 μm.

26. The process of claim 20 wherein the catalyst particle should have a particle size distribution in which 100% of the particles are less than 35 μm and 100% of the particles are greater than 0.7 μm.

27. The process of claim 26 wherein the catalyst particle size distribution is such that the particles in the 50 percentile of the particle size distribution are in the range of 4–7 μm and the area mean diameter of the particles are in the range of 3.0 to 5.5 μm.

28. The process of claim 27 wherein the halogen of the organohalide is chlorine.

29. The process of claim 28 wherein the organohalide has the formula, RCl, where R is selected from the class consisting of alkyl radicals of 1–8 carbon atoms, phenyl radicals, alkenyl radicals of 2–8 carbon atoms.

30. The process of claim 29 wherein the organohalide is methyl chloride and is present in the form of a gas.

31. The process of claim 30 where the silicon metal is present in the form of particles having a size in the range of 10–700 μm.

32. The process of claim 31 wherein the silicon metal particles have an average size distribution of greater than 20 μm and less than 300 μm.

33. The process of claim 32 wherein the reaction is carried out at a temperature of 250°–350° C.

34. The process of claim 33 wherein the process is carried out at a pressure of 1–10 atmospheres above atmospheric pressure.

35. The process of claim 34 wherein the catalyst particles and the silicon metal particles are present in the reactor as a fluidized bed and an organohalide gas is passed therethrough and a product stream is removed from the fluidized bed of unreacted organohalides and organohalosilanes.

36. The process of claim 35 wherein the organohalosilane reaction product stream, the main constituents are organotrihalosilanes and diorganodihalosilanes where the weight ratio of organotrihalosilanes to diorganodihalosilanes is less than 0.2 where organo is as previously defined.

37. The process of claim 36 wherein the weight ratio of organotrihalosilanes to diorganohalosilane in the product stream is less than 0.1.

38. The process of claim 37 wherein the product stream or organohalosilanes is passed through particle entrapment units to remove particles of silicon and catalyst which particles are returned to the reactor and where the product stream is then condensed and distilled to purify different fractions of organohalosilanes that are produced in the process.

39. The process of claim 38 wherein the particle size entrapment units are cyclone particle separators.

* * * * *

UNITED STATES PATENT AND TRADEMARK OFFICE
CERTIFICATE OF CORRECTION

PATENT NO. : 4,450,282
DATED : May 22, 1984
INVENTOR(S) : A. Ritzer and H. Lapidot It is certified that error appears in the above-identified patent and that said Letters Patent are hereby corrected as shown below:

Claim 1, Line 3   After "with" insert -- silicon --.

Signed and Sealed this

Twelfth Day of February 1985

[SEAL]

Attest:

DONALD J. QUIGG

Attesting Officer    Acting Commissioner of Patents and Trademarks